(12) United States Patent
Ansari

(10) Patent No.: US 11,473,048 B2
(45) Date of Patent: Oct. 18, 2022

(54) BIOREACTORS AND METHODS FOR PROCESSING BIOLOGICAL MATERIAL

(71) Applicant: NORTHWICK PARK INSTITUTE FOR MEDICAL RESEARCH LTD, Greater London (GB)

(72) Inventor: Tahera Iqbal Ansari, Greater London (GB)

(73) Assignee: VIDEREGEN LIMITED, Liverpool (GB)

( * ) Notice: Subject to any disclaimer, the term of this patent is extended or adjusted under 35 U.S.C. 154(b) by 933 days.

(21) Appl. No.: 16/321,983

(22) PCT Filed: Jul. 25, 2017

(86) PCT No.: PCT/GB2017/052171
§ 371 (c)(1),
(2) Date: Jan. 30, 2019

(87) PCT Pub. No.: WO2018/025012
PCT Pub. Date: Feb. 8, 2018

(65) Prior Publication Data
US 2019/0177680 A1      Jun. 13, 2019

(30) Foreign Application Priority Data

Aug. 3, 2016   (GB) ..................... 1613410

(51) Int. Cl.
| C12M 1/00 | (2006.01) |
| C12M 3/00 | (2006.01) |
| C12M 1/12 | (2006.01) |

(52) U.S. Cl.
CPC ............ *C12M 29/10* (2013.01); *C12M 21/08* (2013.01); *C12M 23/06* (2013.01); *C12M 25/14* (2013.01); *C12M 29/26* (2013.01)

(58) Field of Classification Search
CPC ...... C12M 25/14; C12M 29/26; C12M 29/10; C12M 21/08; C12M 23/06
See application file for complete search history.

(56) References Cited

U.S. PATENT DOCUMENTS 5,792,603 A * 8/1998 Dunkelman ............ A61F 2/062
                                              435/284.1
5,882,929 A    3/1999 Fofonoff et al.
(Continued)

FOREIGN PATENT DOCUMENTS

| CN | 101837151 A | 9/2010 |
| JP | 0646832 A | 11/1993 |

(Continued)

OTHER PUBLICATIONS

International Search Report for PCT/GB2017/052171 filed Jul. 25, 2017.
(Continued)

*Primary Examiner* — Sean C. Barron
(74) *Attorney, Agent, or Firm* — Notaro, Michalos & Zaccaria P.C.

(57) ABSTRACT

A bioreactor including a housing, a first fluid dispenser and a second fluid dispenser. The bioreactor is configured to receive a scaffold mounted within the housing with the first and second fluid dispensers being positioned to apply respective first and second fluids to at least two different regions of a mounted scaffold.

18 Claims, 4 Drawing Sheets

(56) References Cited

U.S. PATENT DOCUMENTS

| | | |
|---|---|---|
| 8,507,263 B2 | 8/2013 | Asnaghi et al. |
| 2010/0093066 A1 | 4/2010 | Taylor et al. |
| 2011/0033918 A1 | 2/2011 | Asnaghi et al. |
| 2011/0212493 A1* | 9/2011 | Hirschel ................ C12M 29/10 |
| | | 435/235.1 |
| 2012/0178155 A1 | 7/2012 | Levesque et al. |
| 2014/0273222 A1 | 9/2014 | Weinberger et al. |

FOREIGN PATENT DOCUMENTS

| | | | |
|---|---|---|---|
| JP | 11504216 A | 10/1996 | |
| JP | 2002315566 A | 1/2004 | |
| JP | 2006311887 A * | 11/2006 | ............ C12M 21/08 |
| JP | 2006311887 A | 11/2006 | |
| WO | 97/39624 | 4/1997 | |
| WO | 03/070084 A2 | 8/2003 | |
| WO | 2006088029 A1 | 11/2007 | |
| WO | 2010/05090 | 7/2009 | |
| WO | 2013071096 A1 | 5/2013 | |
| WO | 2014/202958 | 6/2014 | |

OTHER PUBLICATIONS

Written Opinion of the International Searching Authority for PCT/GB2017/052171 filed Jul. 25, 2017.

* cited by examiner

BIOREACTORS AND METHODS FOR PROCESSING BIOLOGICAL MATERIAL

TECHNICAL FIELD OF THE INVENTION

The present invention relates to improvements in or relating to bioreactors and methods for processing biological material using an improved bioreactor.

BACKGROUND TO THE INVENTION

It is known to use bioreactors to process tissues in vitro for subsequent transplant into a patient. For example, bioreactors are commonly used to form tubular tissues such as a trachea, blood vessel, oesophagus, or intestine, or at least a section of such tissues. Such structures are typically formed from a scaffold, which may be an artificial scaffold but is commonly of the form of a decellularised equivalent tissue type. The bioreactor is used to seed and grow one or more cell types on or in one or more surfaces of the formed scaffold. This is typically achieved by applying a liquid biological medium to the scaffold, generally by bathing the scaffold in the medium.

Known bioreactors typically comprise a central axle within a housing on which the tubular scaffold may be mounted. The liquid medium is then introduced into the housing of the bioreactor to submerge at least part of the scaffold within the liquid medium. In order to ensure that the whole of the tubular scaffold is submerged within the liquid medium, the scaffold is typically rotated about the central axle. An exemplary apparatus is shown in U.S. Pat. No. 8,507,263. The bioreactor illustrated in this document includes a central shaft defining the central axle wherein the shaft is additionally operable to supply a liquid medium into the interior of the housing for submerging the scaffold.

However, bioreactors of this type suffer a number of drawbacks. Submerging the scaffold in the liquid medium can prevent differentiation of cell types on the surfaces of the scaffold. For example, in some instances it is necessary for the cell types grown on the interior surface of a tubular scaffold to be of a different type to those grown on the exterior surface of the same scaffold. This cannot be readily achieved with known bioreactors which submerge the scaffold as the interior of the scaffold is flooded with the same medium as the exterior. U.S. Pat. No. 8,507,263 attempts to address this by using the scaffold to define inner and outer chambers and supplying different fluids to the two chambers. However, it is common for the scaffold to be porous for the interior space of the scaffold to be fluidly connected with the outside of the scaffold and therefore the two different fluid types would necessarily mix in such instances.

Another drawback of submersion bioreactors is that once the liquid medium/media has been introduced into the bioreactor housing it cannot be re-oxygenated and/or is retained in the bioreactor for a substantial period of time before it is recycled and/or re-oxygenated. An extended period without re-oxygenation can be detrimental to the cells contained within the medium/media.

It would therefore be advantageous to provide a bioreactor which applies a medium/media to one or more surfaces of a scaffold without submerging the scaffold (or at least part of the scaffold) within the medium/media.

It would also be advantageous to provide a bioreactor which is able to re-oxygenate the liquid medium/media during the seeding/growing process.

It would also be advantageous to provide a bioreactor in which different cell types can be seeded onto the inside and outside surfaces of a tissue scaffold, and substantially retain segregation of the different cell types.

It is therefore an aim of an embodiment or embodiments of the present invention to overcome or at least partially mitigate the problems associated with the prior art.

SUMMARY OF THE INVENTION

According to a first aspect of the present invention there is provided a bioreactor comprising a housing, a first fluid dispenser and a second fluid dispenser; the bioreactor being configured to receive a scaffold mounted within the housing with the first and second fluid dispensers being positioned to apply first and second fluids to at least two different regions of a mounted scaffold.

The bioreactor may comprise a fluid outlet for removing fluid from within the housing.

By providing an outlet for removal of fluid from within the housing this prevents a mounted scaffold being submerged, or at least partially submerged, within the fluid which is supplied to its surfaces. Flooding of the mounted scaffold may prevent cell differentiation on the scaffold. The fluid outlet of the bioreactor of the present invention prevents fluid collecting within the housing and flooding the mounted scaffold, in use.

By providing two different fluid dispensers, it is possible to provide different media to different surfaces or regions of a scaffold, especially the interior and exterior surfaces of the scaffold. This allows different cell types, growth factors and other components to be applied to different areas in order to enable differential growth and/or optimal growth conditions in each area.

The first and second fluid dispensers may be positioned to apply fluid to different portions of the same surface of a mounted scaffold. In other embodiments the first and second fluid dispensers may be positioned to apply fluid to different surfaces of a mounted scaffold.

The first and second fluid dispensers may comprise one or more fluid apertures, from which the fluid is dispensed. The first and second fluid dispensers may comprise first and second shafts or conduits.

In some embodiments the first fluid dispenser may be positioned to apply a first fluid to an interior surface of a mounted scaffold. In some embodiments the second fluid dispenser may be positioned to apply a second fluid to an exterior surface of a mounted scaffold. In presently preferred embodiments the first fluid dispenser is positioned to apply a first fluid to an interior surface of a mounted scaffold and the second fluid dispenser is positioned to apply a second fluid to an exterior surface of a mounted scaffold.

By providing a first fluid dispenser for applying a first fluid to an interior surface of a mounted scaffold and a second fluid dispenser for applying a second fluid to an exterior surface of a mounted scaffold, the bioreactor of the invention provides a means to independently choose the fluid applied to either surface. For example, in many instances it may be desirable that the cell types to be grown on the interior and exterior surfaces of the scaffold are different.

In some embodiments the bioreactor may be operable to recycle the fluid removed through the fluid outlet. For example, in some embodiments the bioreactor may comprise one or more pipelines to direct the removed fluid to the first and/or second fluid dispensers for reapplying the fluid to one or more regions or surfaces of a mounted scaffold. Recycling fluid removed from the bioreactor reduces waste and therefore improves the efficiency of the bioreactor.

In some embodiments the bioreactor may comprise, or comprise means for connecting the bioreactor to, one or more oxygenators. The or each oxygenator may be operable in use to oxygenate the first and/or second fluid before it is applied to a region surface of a mounted scaffold through the first or second fluid dispenser. In some embodiments the bioreactor may comprise, or comprise means for connecting the bioreactor to, one or more oxygenators operable in use to re-oxygenate fluid removed through the fluid outlet. In such embodiments, the bioreactor may comprise, or comprise means for connecting the bioreactor to, one or more oxygenators within at least one of one or more pipelines between the fluid outlet and the first and/or second fluid dispenser.

In some embodiments the bioreactor may comprise, or comprise a means for connecting the bioreactor to, a first reservoir within which is contained the first fluid. In such embodiments, the bioreactor may comprise, or comprise a means for connecting the bioreactor to, one or more pipelines to supply the first fluid from the first reservoir to the first fluid dispenser. The bioreactor may additionally comprise, or comprise a means for connecting the bioreactor to, a first pump for supplying the first fluid to the first fluid dispenser under pressure.

In some embodiments the bioreactor may comprise, or comprise a means for connecting the bioreactor to, a second reservoir within which is contained the second fluid. In such embodiments, the bioreactor may comprise, or comprise a means for connecting the bioreactor to, one or more pipelines to supply the second fluid from the second reservoir to the second fluid dispenser. Alternatively, the bioreactor may be configured such that the second fluid is supplied to the second fluid dispenser from the fluid outlet, only. In such embodiments, the bioreactor may comprise, or comprise means for connecting the bioreactor to, one or more oxygenators between the fluid outlet and the second fluid dispenser operable in use to re-oxygenate fluid removed through the fluid outlet to form the second fluid. The bioreactor may additionally comprise, or comprise a means for connecting the bioreactor to, a second pump for supplying the second fluid, from a second reservoir or from the fluid outlet, to the second fluid dispenser under pressure.

In further embodiments the first and second fluids may be the same. In such embodiments the bioreactor may comprise, or comprise a means for connecting the bioreactor to, a single reservoir. The bioreactor may comprise, or comprise a means for connecting the bioreactor to, one or more pipelines for supplying fluid from the single reservoir to the first fluid dispenser, and may comprise, or comprise a means for connecting the bioreactor to, one or more further pipelines for supplying fluid from the single reservoir to the second fluid dispenser.

The first and/or second fluid dispenser may comprise a perforated shaft or conduit having one or more holes therein. The one or more holes are preferably in fluid communication with a bore through the shaft or conduit within which the first or second fluid may be supplied, in use. The first and/or second shafts or conduits may be operable to apply the first or second fluid onto one or more regions or surfaces of a mounted scaffold through said one or more holes within the shaft or conduit.

The bioreactor may comprise a support structure onto which a scaffold may be mounted, in use. The support structure may preferably be provided at least partly within the housing of the bioreactor. The support structure may be configured such that a scaffold may be rotatably mounted thereon. In some embodiments the support structure itself may be rotatable, with the rotation of the support structure causing a simultaneous rotation of a mounted scaffold, in use.

In presently preferred embodiments the bioreactor is configured to receive a tubular scaffold which, when mounted, is rotatable about an axis running through the centre of the tubular scaffold. In such embodiments the first fluid dispenser, which may be a first shaft or conduit, of the bioreactor may be provided parallel with the axis of rotation of a mounted scaffold. In presently preferred embodiments the first fluid dispenser, which may be a first shaft or conduit, of the bioreactor is provided along the axis of rotation of a mounted scaffold. In such embodiments, a scaffold, when mounted within the bioreactor, is coaxial with and surrounds the first fluid dispenser. In this way, the bioreactor provides a means to apply a first fluid onto an interior surface of a mounted scaffold. By rotating a tubular scaffold through a full 360° about a central axis, the entire interior surface of the tubular scaffold may be coated with a first fluid from the first fluid dispenser, in use.

In some embodiments the first fluid dispenser may form part of the support structure and the support structure may comprise the first fluid dispenser, which may be a first shaft or conduit. In such embodiments the support structure, and hence the first fluid dispenser along with a mounted scaffold, may be rotatable about a central axis, in use. Preferably, the central axis is defined by the first fluid dispenser.

The scaffold, central axis and/or first fluid dispenser may be arranged to rotate at between 1 revolution per 30 seconds and 1 revolution per 30 minutes, for example, such as 1 revolution per minute, 1 revolution per 2 minutes, 1 revolution per 2.5 minutes or 1 revolution per 5 minutes.

The interior of the housing, the first and second fluid dispenser, the tubular scaffold and the first and second fluids may all independently be maintained at a temperature of between 20° C. and 45° C., especially between 30° C. and 40° C., such as around 37° C., for example.

The atmosphere within the housing may be controlled to vary the levels of $CO_2$, oxygen and nitrogen, as required, for example to maintain normic or hypoxic atmospheres, depending on the biological materials being used.

The second fluid dispenser may be spaced apart from the first fluid dispenser and may be positioned directly above the position of a scaffold when mounted within the housing of the bioreactor. In this way, the second fluid may be applied to an exterior surface of a mounted scaffold under gravity. For example, the second fluid may drip or be sprayed through one or more holes within the second fluid dispenser onto an exterior surface of a mounted scaffold, in use. In embodiments wherein a tubular scaffold may be rotatably mounted within the housing of the bioreactor, the second fluid dispenser may be operable in use to coat the entire exterior surface of a mounted scaffold through rotation of the scaffold through a full 360° about a central axis through the tubular scaffold.

The housing of the bioreactor may be in the form of an elongate prism having opposing end surfaces. Preferably, the housing of the bioreactor is cylindrical and has circular opposing end surfaces. The housing comprises a cavity within which the first and second fluid dispensers are at least partly located. The cavity may comprise any shape but is preferably complementary to the housing itself. For example, in some embodiments the housing comprises a cylindrical shape having a cylindrical cavity therein.

The first and/or second fluid dispensers may be provided and/or extend through an opening in the housing. In this way, the bioreactor is configured such that the first and/or second fluid dispensers are at least partly located within the housing. Alternatively, the first and/or second fluid dispensers may be connected to one or more pipelines for supplying fluid thereto at an opening in the housing. In such embodiments, the first and/or second fluid dispensers may be entirely located within the housing and connectable to a source of fluid at an opening within the housing. The bioreactor may comprise one or more O-ring seals about the opening to ensure a liquid-tight and preferably a fluid-tight seal about the opening to prevent unwanted leakage of liquid or fluid from within the housing. In presently preferred embodiments, the first and/or second fluid dispensers are provided through or connected to one or more pipelines for supplying fluid thereto at an opening within at least one of the end surfaces of the housing. In some embodiments the first fluid dispenser is provided through or connected to one or more pipelines for supplying fluid thereto at a first opening in a first end surface of the housing. Additionally or alternatively, the second fluid dispenser is provided through or connected to one or more pipelines for supplying fluid thereto at a second opening in a second end surface of the housing.

According to a second aspect of the present invention there is provided a bioreactor comprising a housing, a first shaft and a second shaft positioned above the first shaft; the bioreactor being configured to receive a scaffold rotatably mounted within the housing coaxial with and about the first shaft, wherein the first shaft is positioned to apply first fluid to a first region on an interior surface of a mounted scaffold, and the second shaft is positioned to apply a second fluid to a second region on an exterior surface of a mounted scaffold; the bioreactor additionally comprises a fluid outlet for removing fluid from within the housing.

The bioreactor of the second aspect of the invention may comprise any or all of the features of a bioreactor in accordance with the first aspect of the invention as is desired or appropriate.

According to a third aspect of the present invention there is provided a bioreactor of the first or second aspect of the invention comprising a scaffold mounted within the housing.

The scaffold may be a tubular scaffold.

In some embodiments the tissue comprises a tissue scaffold and the tissue scaffold may comprise at least a section of biological tissue or a section of an organ. The biological tissue/organ section may be decellularised. In other embodiments, the scaffold may comprise a synthetic scaffold adapted to enable cell or tissue growth thereon and/or therein, and/or be adapted to mimic biological tissue.

Suitable tissues or organ sections may be selected from interstitial, connective or supporting tissue, which may be cartilaginous, fibrocartilaginous or calcified cartilaginous tissue, for example bowel, trachea, oesophagus, blood vessel, stomach, urethra, bladder, lung, liver, spleen, kidney, larynx, synovial membrane, tendon, bone-tendon, bone-ligament or ligament, for example. Alternatively the tissue may be dermal tissue.

The tissue scaffold may comprise any suitable tissue which has been decellularised according to any suitable process, in order to substantially remove cellular material from the tissue and form the tissue scaffold. Decellularisation may be performed by using the processes described in WO2014/202958, for example.

Alternatively, decellularisation may be effected by subjecting the biological tissue to a decellularisation process comprising subjecting the tissue to osmotic shock. The decellularisation process may comprise contacting the tissue sequentially with hypotonic and hypertonic solutions (in any order) to promote cell lysis.

The biological tissue may be immersed in the hypotonic and hypertonic solutions. Contact, or immersion, of the biological tissue with the hypotonic and hypertonic solutions may be repeated at least once, and preferably at least twice, three times or four times. The hypertonic solution may comprise sodium chloride. The hypertonic solution may further comprise ethylenediaminetetracetate (EDTA) and/or Tris-HCl. The hypertonic solution may comprise between 0.5M and 2M NaCl, such as around 1M NaCl. The EDTA may be present at a concentration of between 10 mM and 100 mM, such as between 20 mM and 50 mM or around 25 mM. The Tris-HCl may be present at a concentration of between 20 mM and 100 mM, such as between 25 mM and 75 mM or around 50 mM. The hypertonic solution may comprise 1M sodium chloride, and optionally 25 mM EDTA and 50 mM Tris-HCl. The hypotonic solution may comprise EDTA and/or Tris-HCl which may be present at concentrations as described for the hypertonic solution described above.

A decellularisation process comprising subjecting the tissue to osmotic shock may also comprise contacting the tissue with one or more nuclease. The nuclease may be contacted with the tissue after the tissue is contacted with the hypotonic and hypertonic solutions. The nuclease may be a DNase or an RNase or a combination of a DNase and RNase. The decellularisation process may also comprise washing the tissue, preferably in a saline solution, such as phosphate buffered saline (PBS), after each step.

According to a fourth aspect of the present invention there is provided a method of processing biological material comprising the steps of:
(a) mounting a scaffold within a housing of a bioreactor;
(b) applying a first fluid from a first fluid dispenser on to a first region of the mounted scaffold; and
(c) applying a second fluid from a second fluid dispenser on to a second region of the mounted scaffold;
and wherein at least one of the first fluid, second fluid and scaffold comprise biological material.

According to a fifth aspect of the present invention there is provided a method of processing biological material using a bioreactor in accordance with the first aspect of the present invention, the method comprising the steps of:
(a) mounting a scaffold within the housing of the bioreactor;
(b) applying a first fluid from the first fluid dispenser of the bioreactor to a first region of the mounted scaffold; and
(c) applying a second fluid from the second fluid dispenser of the bioreactor to a second region of the mounted scaffold;
and wherein at least one of the first fluid, second fluid and scaffold comprise biological material.

In some embodiments of the fourth or fifth aspect of the invention, at least the scaffold comprises biological material, and in preferred embodiments at least the scaffold and one or both of the first and second fluids comprise biological material.

The methods of the fourth or fifth aspects of the invention may comprise growing biological tissue on a scaffold, which may comprise applying cells and/or tissue growth materials to the scaffold. The cells and/or tissue growth materials may be present within the first and/or second fluids.

In the method of the fourth or fifth aspects of the invention, the first and second regions may be located on the same surface of the scaffold, but in preferred embodiments, the first and second regions are located on different surfaces of the scaffold. One of the first region or second region is preferably an interior surface of the scaffold and the other of the second region or first region is preferably an exterior surface of the scaffold.

The method of the fourth or fifth aspects of the invention may comprise processing biological material comprising a biological tissue scaffold which may take any form. Preferably, the method comprises processing biological material on a tubular scaffold.

In some embodiments the method of the fourth or fifth aspects of the invention may comprise forming the scaffold before it is mounted within the housing of the reactor. In such embodiments, the method may comprise forming a scaffold from a section of biological tissue or a section of an organ, for example. The method may additionally comprise the step of decellularising the tissue/organ.

Suitable tissues or organ sections may be selected from interstitial, connective or supporting tissue, which may be cartilaginous, fibrocartilaginous or calcified cartilaginous tissue, for example bowel, trachea, oesophagus, blood vessel, stomach, urethra, bladder, lung, liver, spleen, kidney, larynx, synovial membrane, tendon, bone-tendon, bone-ligament or ligament, for example. Alternatively the tissue may be dermal tissue.

The tissue scaffold may comprise any suitable tissue which has been decellularised according to any suitable process, in order to substantially remove cellular material from the tissue and form the tissue scaffold. Decellularisation may be performed by using the processes described in WO2014/202958, for example.

Alternatively, decellularisation may be effected by subjecting the biological tissue to a decellularisation process comprising subjecting the tissue to osmotic shock. The decellularisation process may comprise contacting the tissue sequentially with hypotonic and hypertonic solutions (in any order) to promote cell lysis.

The biological tissue may be immersed in the hypotonic and hypertonic solutions. Contact, or immersion, of the biological tissue with the hypotonic and hypertonic solutions may be repeated at least once, and preferably at least twice, three times or four times. The hypertonic solution may comprise sodium chloride. The hypertonic solution may further comprise ethylenediaminetetracetate (EDTA) and/or Tris-HCl. The hypertonic solution may comprise between 0.5M and 2M NaCl, such as around 1M NaCl. The EDTA may be present at a concentration of between 10 mM and 100 mM, such as between 20 mM and 50 mM or around 25 mM. The Tris-HCl may be present at a concentration of between 20 mM and 100 mM, such as between 25 mM and 75 mM or around 50 mM. The hypertonic solution may comprise 1M sodium chloride, and optionally 25 mM EDTA and 50 mM Tris-HCl. The hypotonic solution may comprise EDTA and/or Tris-HCl which may be present at concentrations as described for the hypertonic solution described above.

A decellularisation process comprising subjecting the tissue to osmotic shock may also comprise contacting the tissue with one or more nuclease. The nuclease may be contacted with the tissue after the tissue is contacted with the hypotonic and hypertonic solutions. The nuclease may be a DNase or an RNase or a combination of a DNase and RNase. The decellularisation process may also comprise washing the tissue, preferably in a saline solution, such as phosphate buffered saline (PBS), after each step.

In some embodiments the method of the fourth or fifth aspect of the invention may comprise rotating the mounted scaffold whilst the first and/or second fluid is applied to a surface or region thereof. The mounted scaffold may be rotated about an axis which runs through the centre of the scaffold. In embodiments wherein the method comprises processing or growing biological material on a tubular scaffold, the axis about which the scaffold is rotated may comprise an axis along the length of the tubular structure. The first or second fluid dispensers may be located within the mounted scaffold and the other of the first or second fluid dispenser may be located outside of the mounted scaffold.

In some embodiments the method of the fourth or fifth aspect of the invention may comprise removing fluid from within the housing of the bioreactor. In such embodiments, the fluid may be removed through a fluid outlet. The method may comprise opening the fluid outlet intermittently to remove fluid from within the housing periodically. Alternatively, the method of the fourth or fifth aspect of the invention may comprise leaving the fluid outlet open at all times such that fluid is constantly drained from within the housing of the bioreactor.

The method of the fourth or fifth aspect of the invention may comprise recycling fluid withdrawn from the housing of the bioreactor. For example, in some embodiments the removed fluid may be directed to the first and/or second fluid dispensers of the bioreactor for application to a surface or region of the mounted scaffold. The method may additionally comprise re-oxygenating the removed fluid after it has been removed through the fluid outlet before it is directed to the first and/or second fluid dispensers. In such embodiments, the method may comprise directing fluid removed from the housing to an oxygenator before the first and/or second fluid dispenser.

The scaffold, central axis and/or first fluid dispenser may be arranged to rotate at between 1 revolution per 30 seconds and 1 revolution per 30 minutes, for example, such as 1 revolution per minute, 1 revolution per 2 minutes, 1 revolution per 2.5 minutes or 1 revolution per 5 minutes.

The interior of the housing, the first and second fluid dispenser, the tubular scaffold and the first and second fluids may all independently be maintained at a temperature of between 20° C. and 45° C., especially between 30° C. and 40° C., such as around 37° C. for example.

The atmosphere within the housing may be controlled to vary the levels of $CO_2$, oxygen and nitrogen, as required, for example to maintain normic or hypoxic atmospheres, depending on the biological materials being used.

The first and/or second fluids may comprise cells, which may, for example, be selected from stem cells, epithelial cells or the like. Fluids dispensed from the first and second fluid dispensers may comprise cell growth media. The cell growth media may independently comprise growth factors and cell growth materials as are known in the art. The cell growth media is generally chosen to match any cells being dispensed in the media. For example, if bronchial cells are dispensed and the first fluid dispenser dispenses bronchial epithelial cells, then the fluid dispensed from the first fluid dispenser may comprise Bronchial Epithelial Cell Growth Media supplied by Lonza, and if the second fluid dispenser dispenses bone marrow mesenchymal stem cells (BM-MSC) then the fluid dispensed from the second fluid dispenser may comprise Dulbecco's Modified Eagle Medium, for example.

The first and second fluid dispensers may dispense fluid out at the same rate or at rates which may differ by up to 10%, 20%, 30%, 40%, 50%, 60%, 70%, 80%, 90% or 100%, for example. The first and second fluid dispensers may dispense fluid at a rate of between 0.1 ml/minute to 1000 ml/minute, such as between 1 ml/minute and 100 ml/minute, or between 5 ml/minute and 25 ml/minute, for example.

The method may comprise initially applying first and second fluids to the scaffold in steps b) and c) which do not comprise cells, for example for a period of up to 30 s, 60 s, 120 s, 5 minutes, 10 minutes, or 30 minutes, followed by applying first and/or second fluids which contain cells. The scaffold may be rotated throughout steps b) and c) when using cell-containing and cell-free fluids.

DETAILED DESCRIPTION OF THE INVENTION

In order that the invention may be more clearly understood an embodiment thereof will now be described, by way of example only, with reference to the accompanying drawings, of which:

Figure 1:
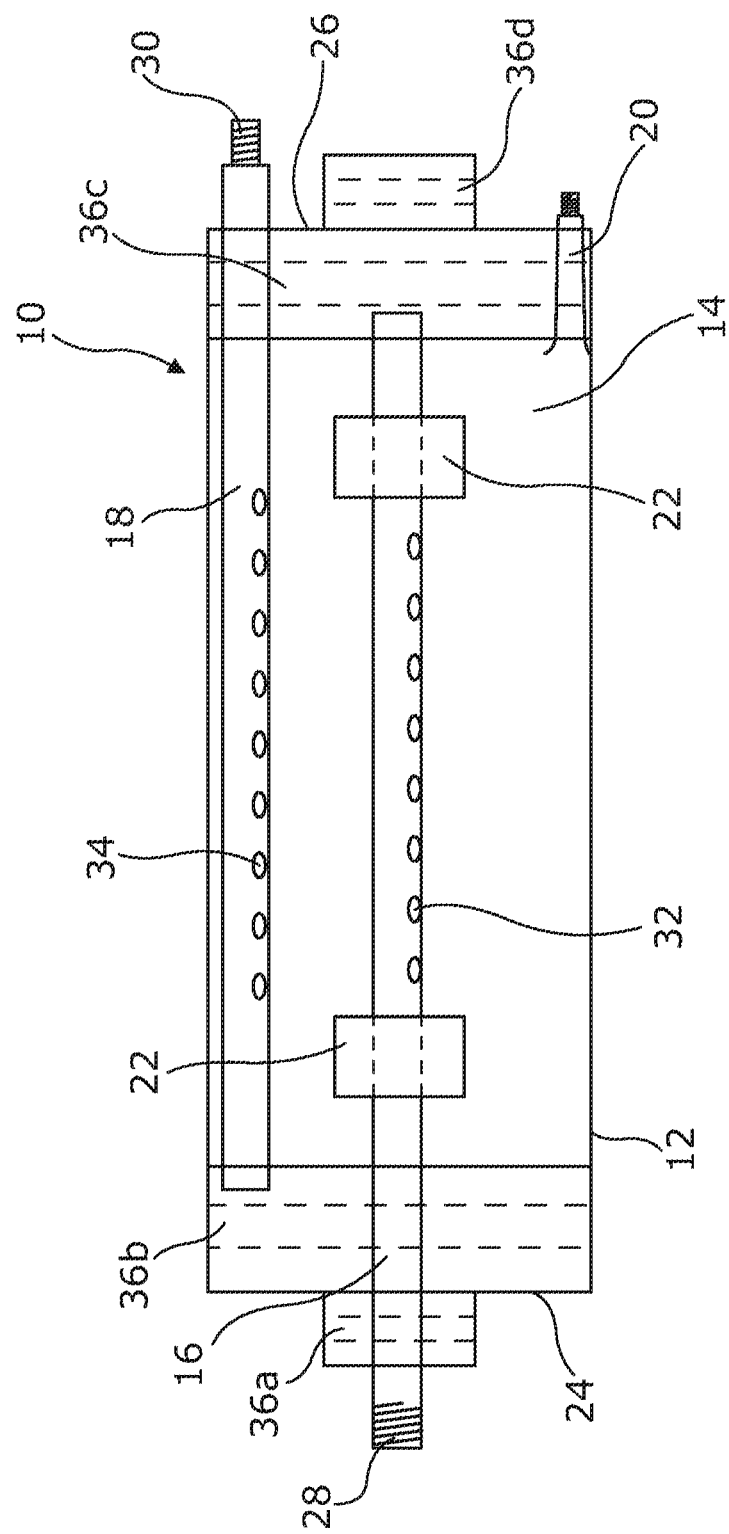
FIG. 1 is a side cross-sectional view of a section of a bioreactor in accordance with the invention.
Figure 2:
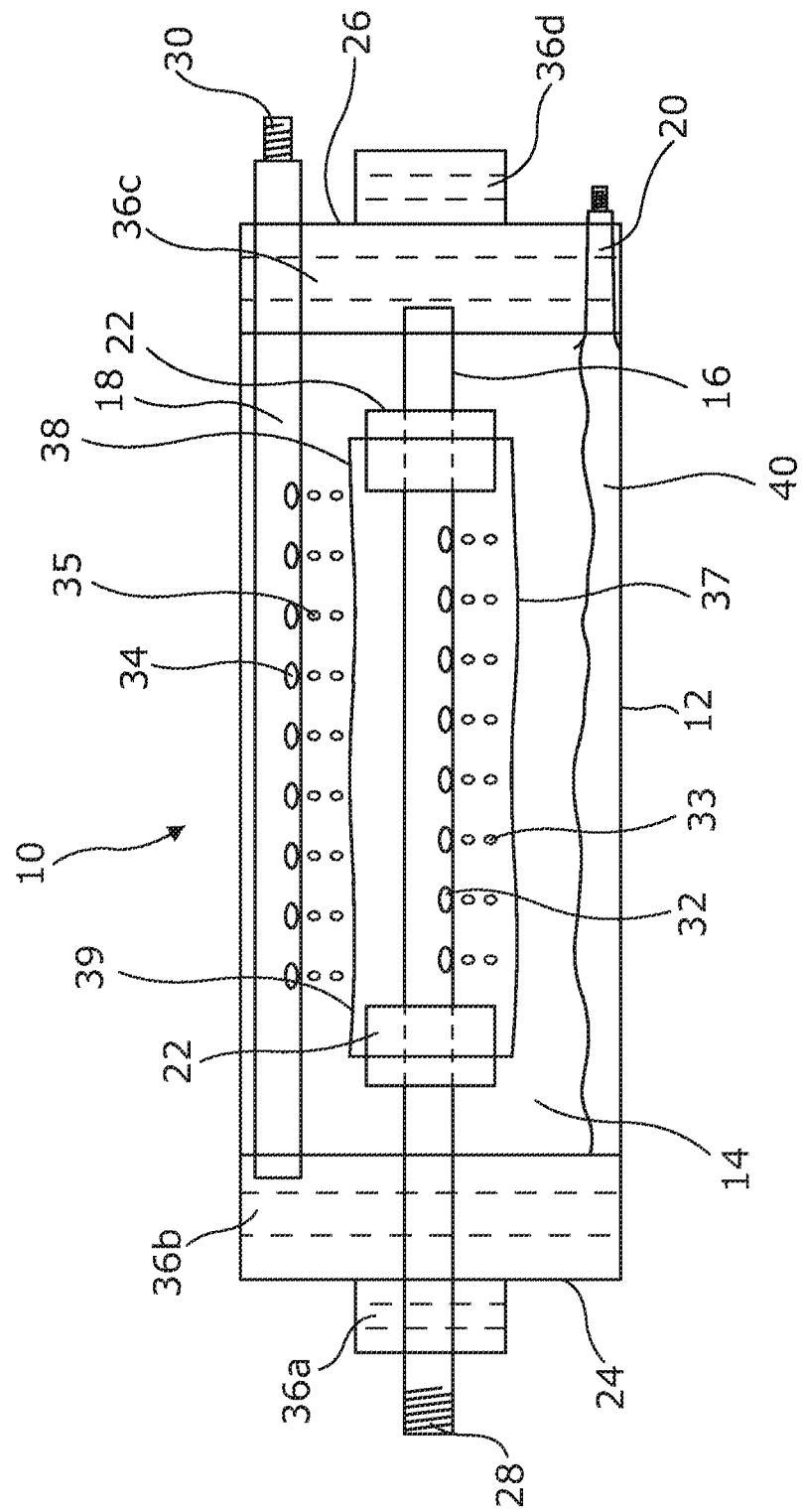
FIG. 2 is a further side cross-sectional view of the section of the bioreactor shown in FIG. 1.

FIGS. 1 and 2 illustrate an exemplary embodiment of a bioreactor 10 in accordance with the invention. The bioreactor 10 includes a housing 12 which is substantially cylindrical and has a cylindrical cavity 14 therein. Within the cavity 14 is located a first fluid dispenser in the form of a first shaft 16 and a second fluid dispenser in the form of a shaft 18. The first shaft 16 is located substantially centrally within the cavity 14 of the housing 12, whereas the second shaft 18 is located near an upper edge of the housing 12 (in the orientation shown in the Figures). As will be described hereinbelow, the shafts 16, 18 are operable in use to apply a fluid onto surfaces of a scaffold 38 mounted within the cavity 14. The bioreactor 10 additionally includes a fluid outlet 20 which may be used to remove fluid from within the cavity 14 of the housing 12, in use, as will be described in detail below.

The bioreactor 10 also comprises a support structure in the form of cylindrical blocks 22. The cylindrical blocks 22 are mounted on the first shaft 16 and are positioned apart along the length of the first shaft 16 towards opposing ends thereof. The blocks 22 are used in the illustrated embodiment to mount a scaffold 38, which will specifically be a tubular scaffold which is substantially cylindrical, within the cavity 14 of the housing 12. Preferably, the blocks 22 are rotatable about an axis defined by the length of the first shaft 16. In this way, a tubular scaffold 38 when mounted on the blocks 22 may also be rotatable about this axis. The position of a tubular scaffold 38 when mounted within the cavity 14 of the housing 12 is shown in FIG. 2.

The tubular scaffold 38 is a biological tissue scaffold that has been decellularised to remove substantially all cellular material. The type of biological tissue is not limited and may be, for example, trachea, oesophagus, bowel or blood vessel, for example.

The first shaft 16 is located mostly within the cavity 14 of the housing 12. However, a portion of the first shaft 16 protrudes out of the housing 12 through an opening in a first end surface 24 of the housing 12. The end of the first shaft 16 protruding from within the housing 12 comprises a fluid connector 28 which acts as both an inlet and outlet for fluid to be introduced or removed from within the first shaft 16. To ensure a fluid-tight seal about the first shaft 16 and at the first end surface 24 of the housing 12, O ring seals 36a, 36b are provided. This prevents unwanted leaks of fluid from within the cavity 14 of the housing 12.

Similarly, the second shaft 18 is located mostly within the cavity 14 of the housing 12. However, a portion of the second shaft 18 protrudes out of the housing 12 through an opening in a second end surface 26 of the housing 12. The end of the second shaft 18 protruding from within the housing 12 comprises a fluid connector 30 which acts as an inlet for fluid to be introduced to the second shaft 18. To ensure a fluid-tight seal about the second shaft 18 and at the second end surface 26 of the housing 12, O ring seals 36c, 36d are provided. Again, this prevents unwanted leaks of fluid from within the cavity 14 of the housing 12.

Each of the first and second shafts 16, 18 are hollow and perforated and comprise a series of holes 32, 34 along their length. As is described below in detail, the holes 32, 34 allow fluid within the shaft 16, 18 to be dispensed from within the shaft 16, 18 onto a surface of a scaffold 38 mounted within the cavity 14 of the housing 12. The holes 32 within the first shaft 16 are provided along the length of the shaft 16 between the blocks 22. Similarly, the holes 34 within the second shaft 18 are provided along the length of the shaft 18, but only along an equivalent length of the shaft 18 as the holes 32 within the first shaft 16. In the orientation shown in the Figures, the holes 34 within the second shaft 18 are provided along the length of the second shaft which is directly above the length of the first shaft 16 which contains holes 32.

As shown in FIG. 2, with the scaffold 38 mounted within the cavity 14 of the housing, the first shaft 16 is positioned centrally through the tubular scaffold 38 such that fluid may be applied to an interior surface 37 of the scaffold 38 through the holes 32 in the shaft 16. In the illustrated embodiment, a first fluid 33 is applied to the interior surface 37 of the scaffold 38 through the holes 32 in the first shaft 16. The second shaft 18 is positioned directly above the tubular scaffold 38 (in the orientation shown in the Figures) such that fluid may be applied to an exterior surface 39 of the scaffold 38 through the holes 34 in the shaft 18. In the illustrated embodiment, a second fluid 35 is applied to the exterior surface 39 of the scaffold 38 through the holes 34 in the second shaft 18.

The first and second fluids 33, 35 may comprise growth media and cells, for example epithelial cells and stem cells respectively in appropriate growth media.

Figure 3:
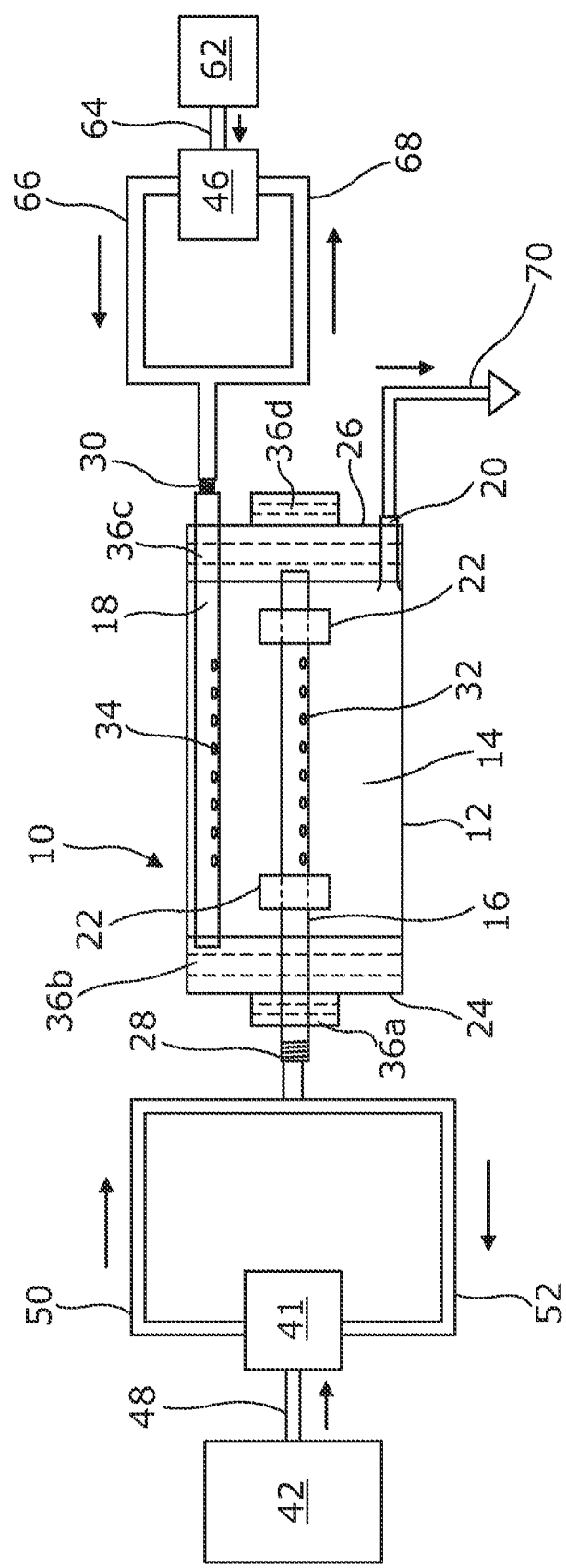
FIG. 3 is a schematic diagram of an operational setup including an embodiment of a bioreactor in accordance with the invention.
Figure 4:
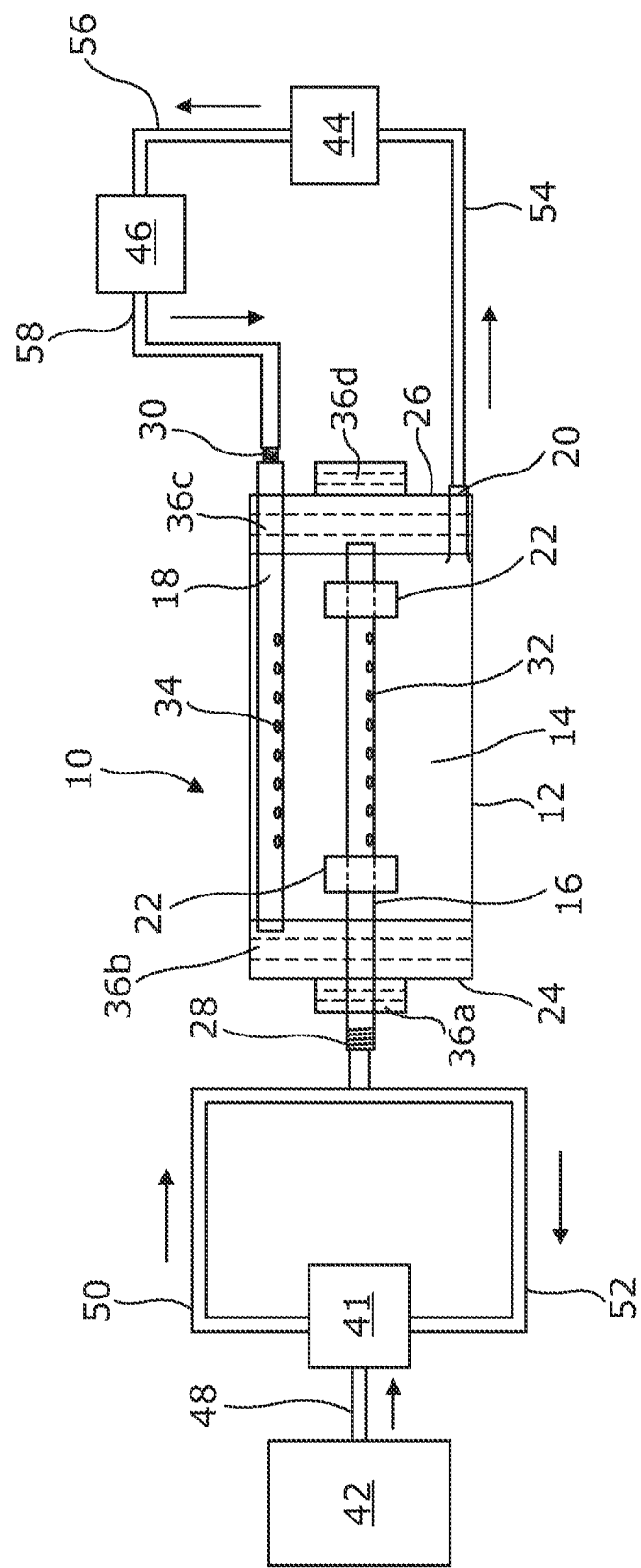
FIG. 4 is a schematic diagram of a further operational setup including an embodiment of a bioreactor in accordance with the invention.

FIGS. 3 and 4 illustrate operational setups which incorporate an embodiment of a bioreactor 10 in accordance with the present invention. In particular, these Figures illustrate how first and second fluids 33, 35 are provided in the respective shafts 16, 18 for application to surfaces of a mounted scaffold 38.

As shown in FIG. 3, the bioreactor 10 is connected to a first pump 41 at the fluid connector 28 at the end of the first shaft 16 via pipelines 50 and 52. Specifically, pipeline 50 is operable to supply fluid from the pump 41 to the fluid connector 28 whereas pipeline 52 is operable to transport fluid from the fluid connector 28 back to the pump 41. The setup shown additionally comprises a first fluid reservoir 42 which is fluidly connected to the pump 41 via pipeline 48.

Similarly, there is also provided a second pump 46 for supplying the second fluid 35 to the second shaft 18 under pressure through fluid connector 30. The second pump 46 is fluidly connected to the fluid connector 30 of the bioreactor 10 through pipelines 66 and 68. Specifically, pipeline 66 is operable to supply fluid from the pump 46 to the fluid connector 30 whereas pipeline 68 is operable to transport fluid from the fluid connector 30 back to the pump 46. The setup shown additionally comprises a second fluid reservoir 62 which is fluidly connected to the pump 46 via pipeline 64.

A waste pipe 70 is provided fluidly connected to the fluid outlet 20 to drain excess fluid from within the housing 12 of the bioreactor 10.

The setup shown in FIG. 4 differs from that shown in FIG. 3 in that the second pump 46 is not supplied with fluid from a reservoir. Rather, the second pump 46 is supplied with fluid obtained through removal of fluid from within the cavity 14 of the housing 12 through fluid outlet 20. In the illustrated embodiment, the bioreactor 10 additionally comprises an oxygenator 44 provided between the second pump 46 and the fluid outlet 20. Specifically, the oxygenator 44 is fluidly connected to the outlet 20 via pipeline 54 and to the second pump 46 via pipeline 56. As will be described below, in such a setup, the oxygenator 44 is operable in use to re-oxygenate fluid removed from within the cavity 14 of the housing 12 such that it can be reused as a second fluid 35 for application to a further surface of a mounted scaffold 38.

The operational use of the bioreactor 10 will now be described with reference to FIGS. 1 to 4.

The bioreactor 10 is used to grow biological material on the surfaces of a scaffold 38 mounted within its housing 12. To achieve this, first and second fluids 33, 35 are applied onto the interior and exterior surfaces 37, 39, respectively. The fluids 33, 35 are applied via respective shafts 16, 18 which protrude into the housing 12. The fluids 33, 35 typically comprise a biological medium containing a plurality of cells which may all be of the same cell type, or may be of two or more different cell types. Preferably, the first and second fluids 33, 35 comprise different biological media. It is, however, to be understood that the first and second fluids 33, 35 could comprise the same media.

In the illustrated bioreactor 10, the first fluid 33 is applied to an interior surface 37 of a mounted scaffold 38 via the first shaft 16. As shown, the scaffold 38 is mounted coaxially about the first shaft 16 within the housing 12 as is positioned such that first fluid 33 contained within the first shaft 16 drips through holes 32 within the first shaft 16 onto the interior surface 37 of the scaffold 38. Whilst the first fluid 33 drips through holes 32 in the first shaft 16, the scaffold 38 is rotated about an axis defined by the first shaft 16 through rotation of the blocks 22 (and in some instances the shaft 16 also). This rotation of the scaffold 38 enables the first fluid 33 to be applied to the entire interior surface 37 of the scaffold 38 upon a full 360° rotation of the scaffold 38 about this axis as the portion of the interior surface 37 located directly below the holes 32 in the first shaft 16 continually changes upon rotation of the scaffold 38.

Similarly, at the same time, the second fluid 35 is applied to an exterior surface 39 of the mounted scaffold 38. To achieve this, the scaffold 38 is mounted directly below the second shaft 18 (in the orientation shown in the Figures) such that second fluid 35 contained within the second shaft 18 drips through holes 34 within the second shaft 18 onto the exterior surface 39 of the scaffold 38. As discussed above, the scaffold 38 is rotated about an axis defined by the first shaft 16 through rotation of the blocks 22 (and in some instances the shaft 16 also). This rotation of the scaffold 38 also enables the second fluid 35 to be applied to the entire exterior surface 39 of the mounted scaffold 38 upon a full 360° rotation of the scaffold 38 about this axis as the portion of the exterior surface 39 located directly below the holes 34 in the second shaft 18 continually changes upon rotation of the scaffold 38.

Excess fluid 40 (which may originate from either the first and/or second shafts 16, 18) will collect underneath the scaffold 38 at the bottom of the cavity 14. This excess fluid 40 is removed from within the cavity 14 through the fluid outlet 20.

In the setup shown in FIG. 3, the removed excess fluid 40 is drained through waste pipe 70 and is not reused. However, in the alternative setup shown in FIG. 4, the removed excess fluid 40 is recycled for use as the second fluid 35 for application to the exterior surface 39 of the mounted scaffold. Specifically, the excess fluid 40 is directed towards an oxygenator 44 subsequent to removal of the fluid 40 through the fluid outlet 20. The oxygenator 44 is operable to re-oxygenate the fluid which is then passed through the second pump 46 to supply the fluid to the second shaft 18 under pressure. This fluid is then applied to the exterior surface 39 of the scaffold 38 as is described above.

In FIG. 4, the fluid 40 removed from within the housing 12 through the fluid outlet 20 is directed back to the second shaft 18. However, it should be understood that the invention is not limited in this sense. Rather, the removed fluid 40 may alternatively be directed to the first shaft 16 for application to the interior surface 37 of the scaffold 38. In further embodiments the removed fluid 40 may be directed to both the first and second shafts 16, 18 for application to both the interior and exterior surfaces 37, 39 of the scaffold 38. In yet further embodiments, such as those using the setup illustrated in FIG. 3, the removed fluid 40 may simply be drained from within the housing 12 and not be reused, as discussed above.

In some embodiments the bioreactor 10 may be connected to a second fluid reservoir as a source of second fluid for application to the scaffold 38, as shown in FIG. 3. In such embodiments, the recovered fluid 40 from within the housing 12 may be used to supplement the first and/or second fluids 33, 35.

In some embodiments the bioreactor 10 may comprise one or more additional oxygenators. For example, in some embodiments the bioreactor 10 may be provided with an oxygenator between the fluid connector 28 and the first pump 41 along pipeline 52. In doing so, fluid which is removed from within the first shaft 16 along pipeline 52 may be re-oxygenated before being pumped back to the first shaft 16 for application to a surface of the mounted scaffold 38.

The above embodiment is described by way of example only. Many variations are possible without departing from the scope of the invention as defined in the appended claims.

The invention claimed is:

1. A bioreactor comprising a housing, a first fluid dispenser and a second fluid dispenser spaced apart from the first fluid dispenser; the bioreactor being configured to receive a scaffold mounted within the housing with the first and second fluid dispensers being positioned to apply respective first and second fluids to at least two different regions of a mounted scaffold, wherein the bioreactor is configured such that, in use, the first fluid dispenser is provided along the axis of rotation of a mounted scaffold, said mounted scaffold being coaxial with and surrounding the first fluid dispenser, and the second fluid dispenser is positioned directly above the position of the mounted scaffold.

2. A bioreactor of claim 1 comprising a fluid outlet for removing fluid from within the housing.

3. A bioreactor of claim 1 wherein the first and second fluid dispensers are positioned to apply fluid to different surfaces of a mounted scaffold.

4. A bioreactor of claim 3 wherein the first fluid dispenser is positioned to apply the first fluid to an interior surface of a mounted scaffold.

5. A bioreactor of claim 3 wherein the second fluid dispenser is positioned to apply the second fluid to an exterior surface of a mounted scaffold.

6. A bioreactor of claim 2 operable to recycle the fluid removed through the fluid outlet.

7. A bioreactor of claim 6 comprising means for connecting the bioreactor to, one or more pipelines to direct the removed fluid to the first and/or second fluid dispensers for reapplying the fluid to one or more surfaces of a mounted scaffold.

8. A bioreactor of claim 1 comprising means for connecting the bioreactor to one or more oxygenators.

9. A bioreactor of claim 8 comprising means for connecting the bioreactor to one or more oxygenators operable in use to re-oxygenate fluid removed through the fluid outlet.

10. A bioreactor of claim 2 configured such that the second fluid is supplied to the second fluid dispenser from the fluid outlet, only.

11. A bioreactor of claim 1 wherein the first and/or second fluid dispenser comprises a perforated shaft or conduit having one or more holes therein.

12. A bioreactor of claim 11 wherein the first and/or second shafts or conduits are operable to apply the first or second fluid onto one or more surfaces of a mounted scaffold through said one or more holes within the shaft or conduit.

13. A bioreactor of claim 1 comprising a support structure onto which a scaffold may be mounted, in use.

14. A bioreactor of claim 13 wherein the support structure is configured such that a scaffold may be rotatably mounted thereon.

15. A bioreactor of claim 1 configured to receive a tubular scaffold which, when mounted, is rotatable about an axis running through the centre of the tubular scaffold.

16. A bioreactor of claim 15 wherein the first fluid dispenser of the bioreactor is provided along the axis of rotation of a mounted scaffold such that a mounted scaffold is coaxial with and surrounds the first fluid dispenser.

17. A bioreactor of claim 1 wherein the second fluid dispenser is positioned directly above the position of a scaffold when mounted within the housing of the bioreactor.

18. A bioreactor of claim 1 comprising a scaffold mounted within the housing.

* * * * *